(12) United States Patent
Jörgensen (10) Patent No.: US 7,992,801 B2
(45) Date of Patent: Aug. 9, 2011

(54) AROMATIC NEBULIZING DIFFUSER

(75) Inventor: Carsten Jörgensen, Kastanienbaum (CH)

(73) Assignee: Ming Jen Hsiao, Miaoli County (TW)

( * ) Notice: Subject to any disclaimer, the term of this patent is extended or adjusted under 35 U.S.C. 154(b) by 112 days.

(21) Appl. No.: 12/552,350

(22) Filed: Sep. 2, 2009

(65) Prior Publication Data

US 2011/0049266 A1 Mar. 3, 2011

(51) Int. Cl.
*B05B 1/08* (2006.01)
*B05B 17/06* (2006.01)

(52) U.S. Cl. .......... 239/102.2; 239/102.1; 239/289; 239/338

(58) Field of Classification Search ........... 239/4, 102.1, 239/102.2, 288, 288.3, 288.5, 289, 302, 337, 239/338, 432; 128/200.14, 200.16, 200.18, 128/200.21; 261/78.1, 78.2, DIG. 48, DIG. 65; 362/96
See application file for complete search history.

(56) References Cited

U.S. PATENT DOCUMENTS

| | | | | |
|---|---|---|---|---|
| 3,901,443 A * | 8/1975 | Mitsui et al. | ........... | 239/102.2 |
| 4,640,804 A * | 2/1987 | Mizoguchi | ........... | 261/81 |
| 4,644,790 A * | 2/1987 | Mizoguchi | ........... | 73/293 |
| 5,881,714 A * | 3/1999 | Yokoi et al. | ........... | 128/200.14 |
| 5,881,715 A * | 3/1999 | Shibasaki | ........... | 128/200.14 |
| 6,543,701 B1 * | 4/2003 | Ho | ........... | 239/102.1 |

* cited by examiner

*Primary Examiner* — Darren W Gorman
(74) *Attorney, Agent, or Firm* — Ming Chow; Sinorica, LLC (57) ABSTRACT

An aromatic nebulizing diffuser includes a base panel, an electric fan, a power control unit, a lower housing, a fluid container that has bottom mounting rods detachably plugged into respective tubular upright posts of the base panel to facilitate cleaning work, a water baffle, an upper housing, an ultrasonic oscillator that controls a light source to emit light when oscillating an aromatic fluid in the fluid container to produce a fine mist of aromatic fluid droplets and a speaker mounted in a vertical speaker holder at the bottom side of the fluid container within the lower housing and controllable by the power control unit for audio output.

9 Claims, 9 Drawing Sheets

AROMATIC NEBULIZING DIFFUSER

BACKGROUND OF THE INVENTION

1. Field of the Invention

The present invention relates to a nebulizing diffuser and more particularly, to an aromatic nebulizing diffuser of high level of safety that provides sound and lighting effects.

2. Description of the Related Art

Regular aromatic nebulizing diffusers or essential oil diffusers commonly use an ultrasonic oscillator to generate a high ultrasonic energy for causing atomization of an essential oil for application. Separation of electric charges in falling rain, caused by breaking up of the water droplets, the drops becoming positively charged and the air negatively charged. This separation of electric charges accompanying the aerodynamic breakup of water drops is known as spray electrification, the waterfall effect or Lenard effect. Conventional aromatic nebulizing diffusers simply produce an upwardly flying mist of aromatic vapor. They cannot simulate the natural visual effect of a flying mist caused by the impact of a waterfall.

Further, conventional essential oil nebulizing diffusers with light emitting means cannot exhibit a lighting effect apparently at daylight. Due to the use of a light-tight housing, conventional essential oil nebulizing diffusers cannot create a colorful mist scenery at night.

Further, conventional aromatic nebulizing diffusers commonly use screws to affix component parts together, complicating mounting and dismounting procedures. After a long use, the inside wall of the aromatic nebulizing diffusers may be covered with a layer of dirt. It takes much time and labor to practice a cleaning work.

Further, the opening of a regular aromatic nebulizing diffuser has a diameter gradually reducing from the inside toward the outside. This gradually reducing diameter design tends to cause the generated fine mist to be condensed into water drops, lowering the fin mist generating performance.

Further, conventional sound-generating aromatic nebulizing diffusers commonly have the speaker and control circuit means mounted in one corner in a horizontal position inside the housing. This arrangement provides poor sound effects.

Further, conventional aromatic nebulizing diffusers may use an electric fan to cause currents of air for flashing an essential oil into a mist. However, due to limited air path, the pressure of the induced currents of air is not sufficient for causing a fine mist in a big area, lower the nebulizing diffusing performance.

Therefore, it is desirable to provide an aromatic nebulizing diffuser that eliminates the drawbacks of the aforesaid conventional designs.

SUMMARY OF THE INVENTION

The present invention has been accomplished under the circumstances in view. It is main object of the present invention to provide an aromatic nebulizing diffuser, which is easily detachable, facilitating cleaning work. It is another object of the present invention to provide an aromatic nebulizing diffuser, which suspends a speaker from a fluid container within a lower housing thereof so that the lower housing works as a sound chamber to enhance output sound, creating better sound effects.

To achieve these and other objects of the present invention, the aromatic nebulizing diffuser comprises a base panel, an electric fan, an ultrasonic oscillator, a power control unit, a lower housing, a fluid container, a speaker, a water baffle and an upper housing. The base panel has a plurality of air vents and a plurality of tubular upright posts. The electric fan is mounted on the base panel corresponding to the air vents. The ultrasonic oscillator with a control circuit function. The ultrasonic oscillator further has a fluid level sensor and a light source arranged on the top side thereof and electrically connected to the ultrasonic oscillator. The power control unit is electrically connected with the electric fan and the ultrasonic oscillator for controlling the operation of the electric fan, the ultrasonic oscillator, the fluid level sensor and the light source. The lower housing surrounds the base panel and defines an accommodation chamber above the base panel for accommodating the power control unit, the electric fan, the ultrasonic oscillator and the speaker.

Further, the power control circuit comprises a circuit board, a power jack mounted on the base panel and electrically connected to the control circuit board for the connection of an external power source, and an audio jack mounted on the base panel and electrically connected to the control circuit board to provide a sound source signal.

Further, the speaker is mounted in a vertical speaker holder at the bottom side of the fluid container inside the lower housing and spaced above the base panel such that the housing works as a sound chamber to enhance output sound.

Further, the base panel comprises a plurality of tubular upright posts, and the fluid container comprises a plurality of bottom mounting rods respectively detachably plugged into the tubular upright posts of the base panel. Thus, the fluid container can easily be detached from the base panel when a cleaning work is necessary. Further, the speaker is mounted in a vertical speaker holder at the bottom side of the fluid container and kept above the base panel at a distance. Thus, the output sound is enhanced in the space inside the lower housing before and then forced out of the lower housing through the air vents of the base panel, creating better sound effects.

Further, the upper housing can be made of ceramic or light-transmissive ceramic to enhance output sound.

Further, the upper housing, the water baffle, the fluid container are preferably made of a transparent or translucent material, such as glass, frosted glass, light-transmissive ceramic, acrylic, plastics or crystal in any of a variety of colors.

Further, the power control unit comprises a circuit board, a power jack mounted on the base panel and electrically connected to the control circuit board for the connection of an external power source and an audio jack mounted on the base panel and electrically connected to the control circuit board to provide a sound source signal.

Further, the fluid container has an air duct disposed inside the fluid chamber for guiding induced currents of air from the electric fan to splash the aromatic fluid in the fluid chamber into a fine mist. The air duct has an air inlet facing the electric fan and an air outlet facing the water baffle, and a diameter gradually reducing in direction from the air inlet toward the air outlet. Thus, when a flow of air goes through the air duct, the pressure of the flow of air is increased to effectively splash the aromatic fluid into a fine mist.

Further, the fluid that is filled in the fluid chamber of the fluid container can be water, essential oil, flower essences, rosemary oil, perfume or natural plant extracts, or their combination.

DETAILED DESCRIPTION OF THE PREFERRED EMBODIMENT

Figure 1:
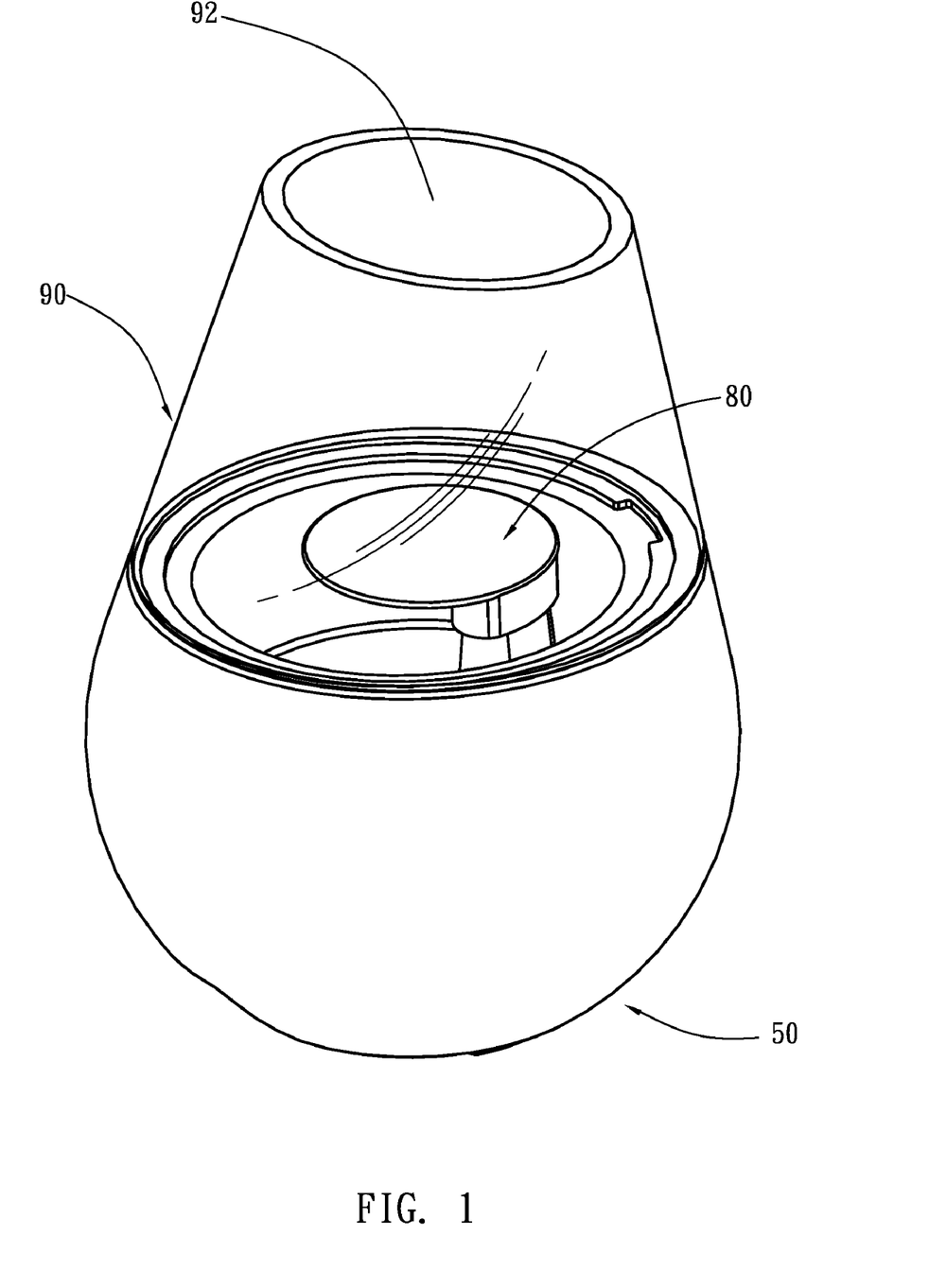
FIG. 1 is a perspective view of an aromatic nebulizing diffuser in accordance with a first embodiment of the present invention.
Figure 2:
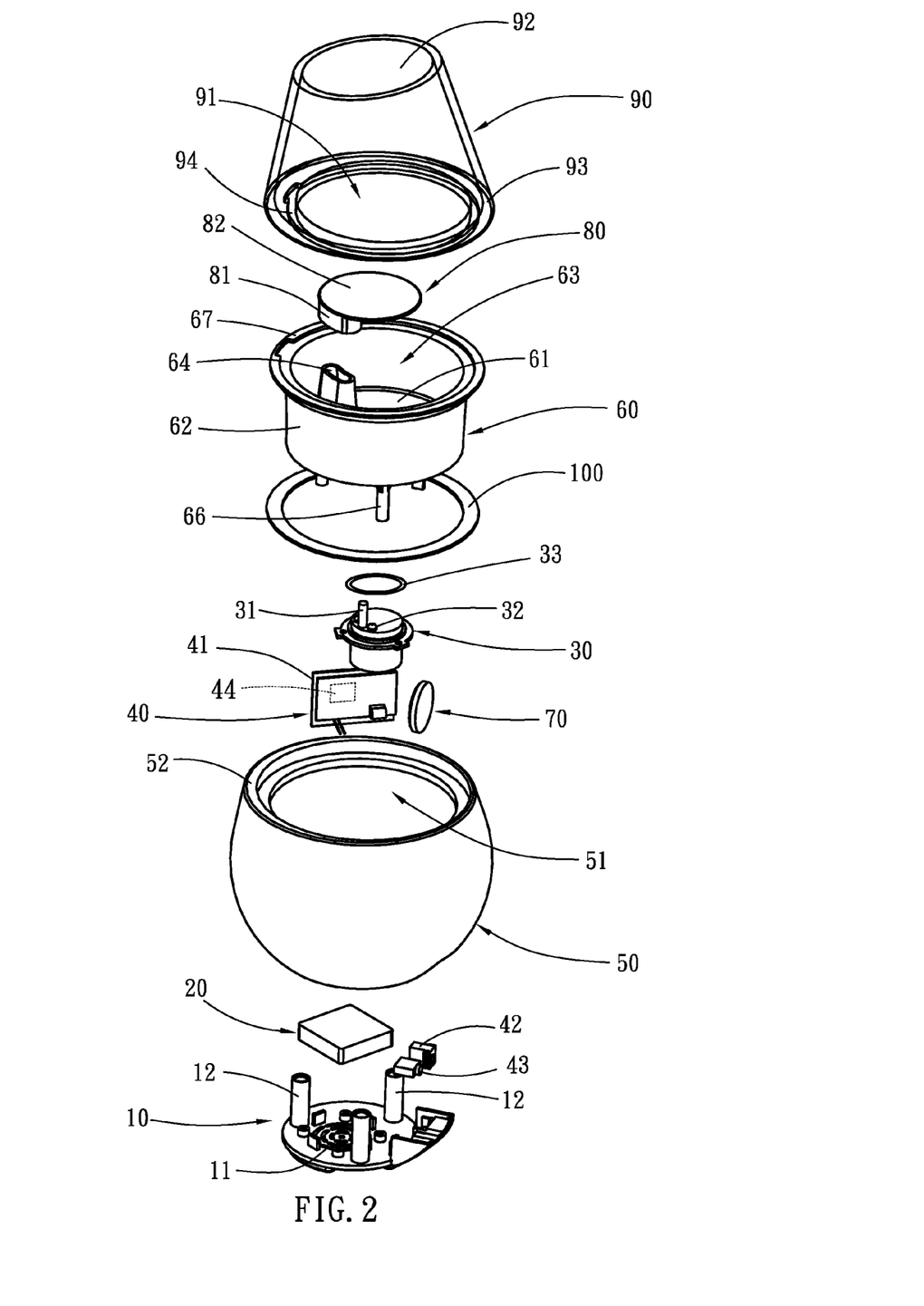
FIG. 2 is an oblique top exploded view of the aromatic nebulizing diffuser in accordance with the first embodiment of the present invention.

Referring to FIGS. 1 and 2, an aromatic nebulizing diffuser in accordance with a first embodiment of the present invention is shown comprising a base panel 10, an electric fan 20, a ultrasonic oscillator 30, a power control unit 40, a lower housing 50, a fluid container 60, a water baffle 80 and an upper housing 90.

Figure 3:
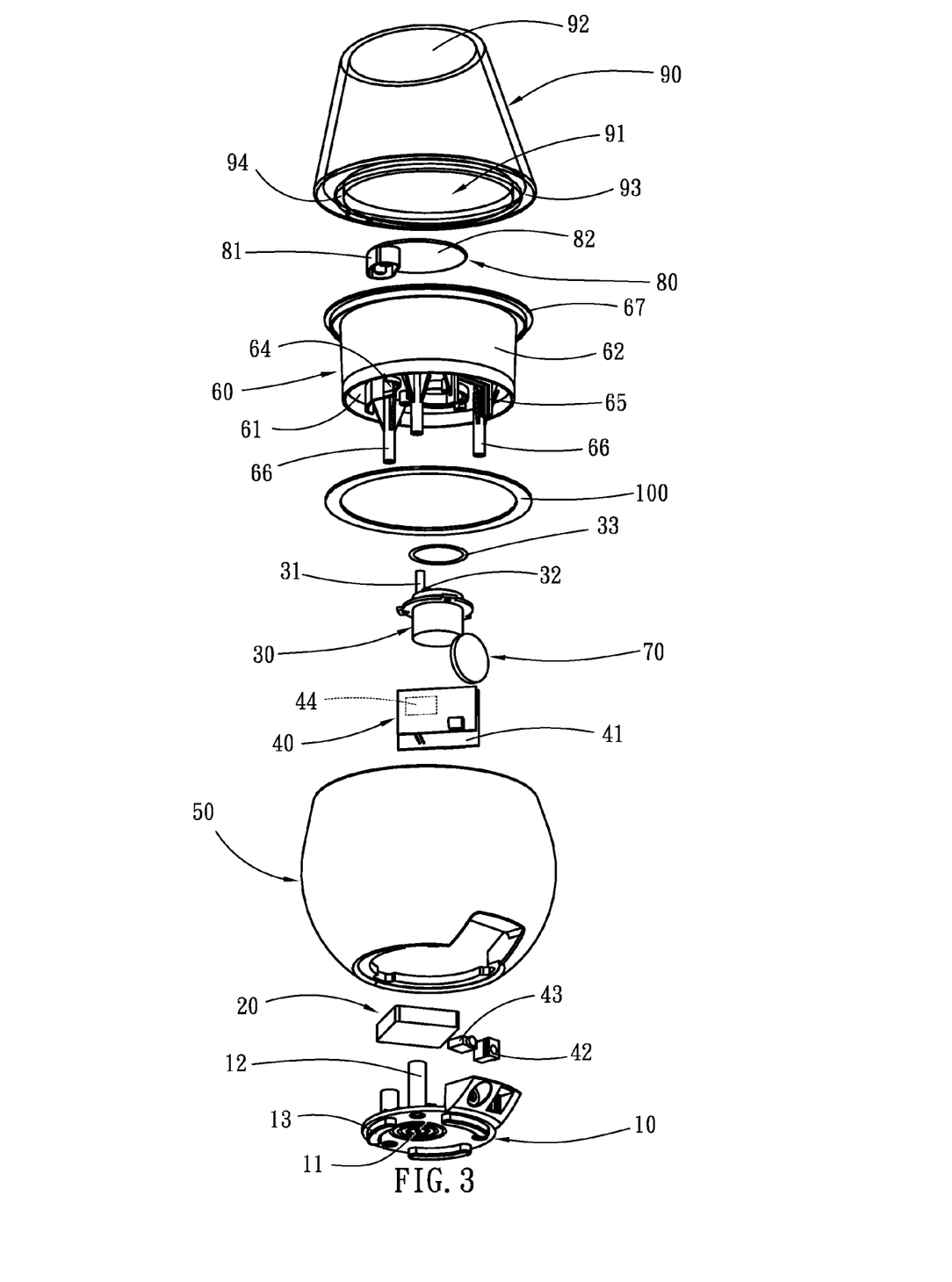
FIG. 3 is an oblique bottom exploded view of the aromatic nebulizing diffuser in accordance with the first embodiment of the present invention.
Figure 4:
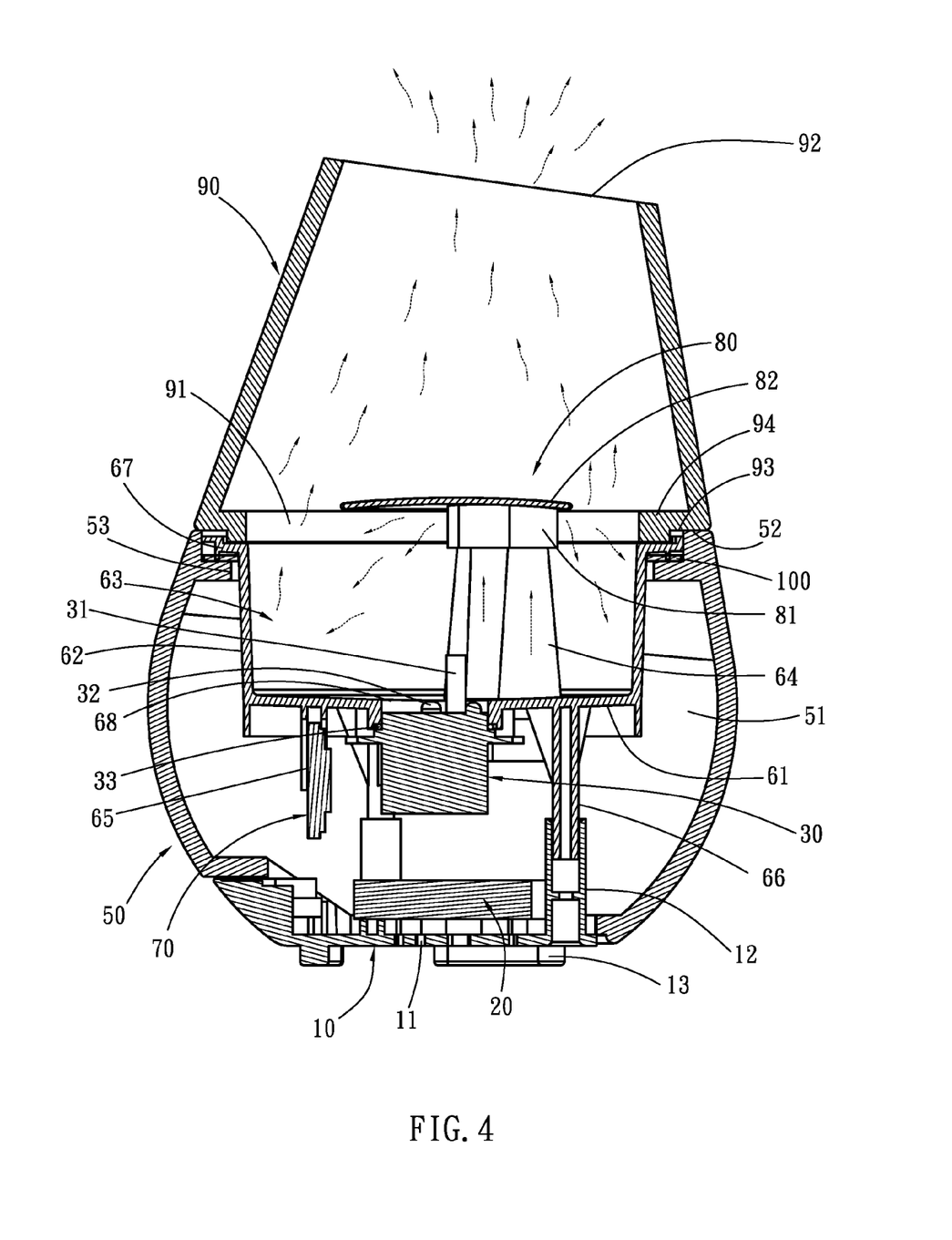
FIG. 4 is a sectional assembly view of the aromatic nebulizing diffuser in accordance with the first embodiment of the present invention.

Referring to FIGS. 3 and 4 and FIG. 2 again, the base panel 10 has a plurality of air vents 11 cut through the top and bottom walls thereof and a plurality of tubular upright posts 12 perpendicularly extended from the top wall.

The electric fan 20 is mounted on the top wall of the base panel 10 corresponding to the air vents 11.

The ultrasonic oscillator 30 with a control circuit function. Further, the ultrasonic oscillator 30 oscillates at a frequency over several hundred thousands of times or several million times per second. A water level sensor 31 and a light source 32 provided at the top side of the ultrasonic oscillator 30. The control circuit function of the ultrasonic oscillator 30 controls on/off of the water level sensor 31 and the light source 32.

The lower housing 50 surrounds the base panel 10, defining an accommodation chamber 51 above the base panel 10 for accommodating the power control unit 40, the electric fan 20 and the ultrasonic oscillator 30. The lower housing 50 has a top rim 52.

The fluid container 60 is accommodated in the accommodation chamber 51 of the lower housing 50 and supported with the topmost edge thereof on an inside step 53 in the accommodation chamber 51 of the lower housing 50. The fluid container 60 comprises a horizontal bottom wall 61, a vertical peripheral wall 62, a fluid chamber 63 surrounded by the horizontal bottom wall 61 and the vertical peripheral wall 62, an air duct 64 suspending in the fluid chamber 63, a plurality of bottom mounting rods 66 perpendicularly downwardly extended from the horizontal bottom wall 61 and respectively detachably plugged into the tubular upright posts 12 of the base panel 10, and a mounting hole 68 cut through the horizontal bottom wall 61 at the center for the mounting of the ultrasonic oscillator 30. By means of the detachable arrangement between the bottom mounting rods 66 of the fluid container 60 and the tubular upright posts 12 of the base panel 10, installation and cleaning works of the fluid container 60 are easy.

Figure 6:
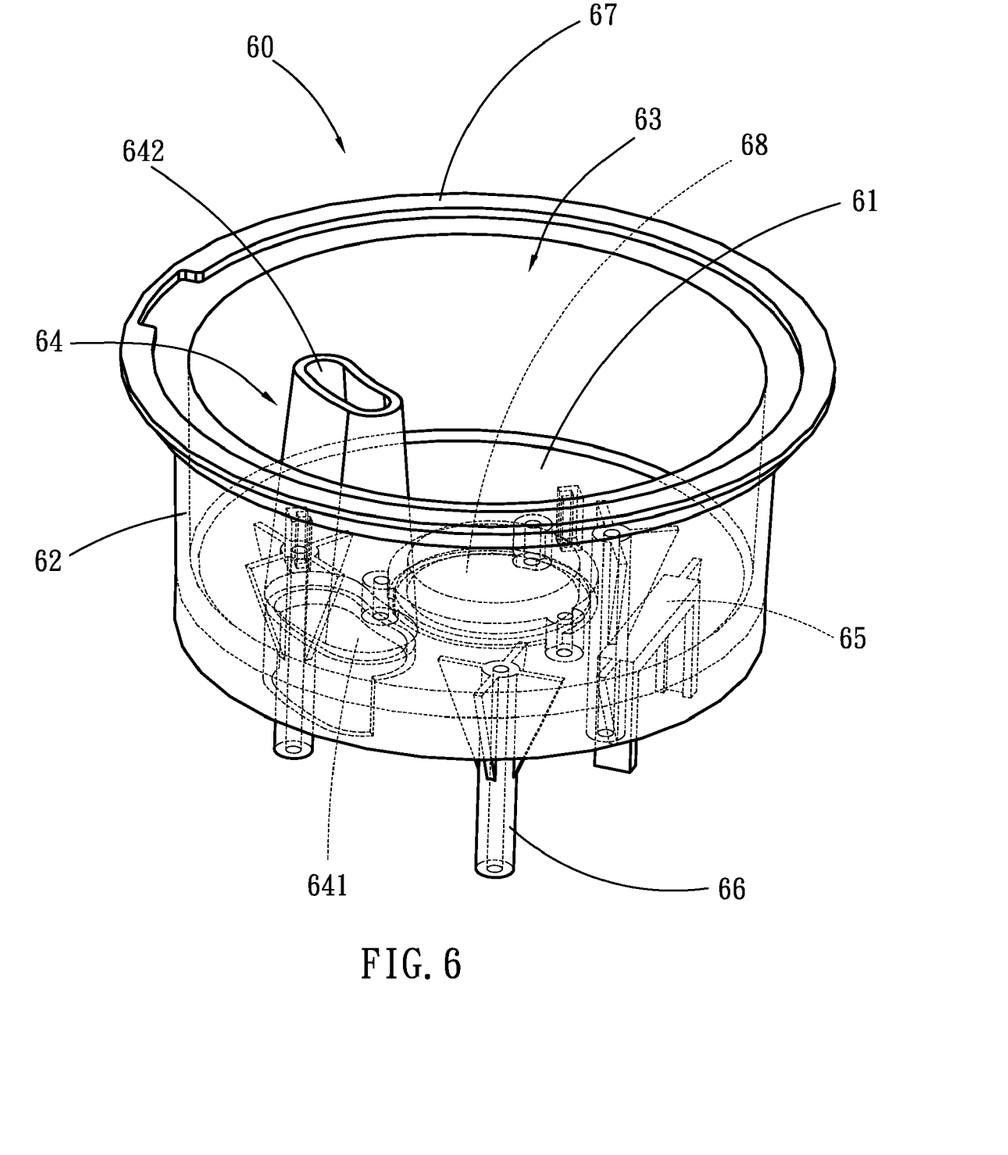
FIG. 6 is a perspective view of the fluid container of the aromatic nebulizing diffuser in accordance with the present invention.

Referring to FIG. 6 and FIG. 4 again, the air duct 64 has an air inlet 641 disposed at the bottom side thereof and inserted into the horizontal bottom wall 61 and facing the electric fan 20 for guiding in currents of air caused by the electric fan 20, an air outlet 642 disposed at the top side thereof, and a diameter gradually reducing in direction from the air inlet 641 toward the air outlet 642. Because the air duct 64 has a diameter gradually reducing in direction from the air inlet 641 toward the air outlet 642, the pressure of air is gradually increased when the currents of air go from the electric fan 20 through the air duct 64.

Further, the fluid container 60 can be made from a transparent or translucent material so that light rays from the light source 32 go through the fluid container 60 and the aromatic fluid in the fluid container 60 to cause visual lighting effects.

The aforesaid ultrasonic oscillator 30 is mounted in the mounting hole 68 on the horizontal bottom wall 61 of the fluid container 60, holding the water level sensor 31 and the light source 32 above the elevation of the horizontal bottom wall 61 of the fluid container 60, i.e., the water level sensor 31 and the light source 32 suspend in the fluid chamber 63. When the fluid lever in the fluid chamber 63 dropped below the elevation of the top side of the water level sensor 31, the water level sensor 31 immediately provides a signal to the control circuit of the ultrasonic oscillator 30, causing the control circuit to cut off power supply from the ultrasonic oscillator 30 or to turn on or off the light source 32, avoiding ultrasonic oscillator damage.

Figure 5:
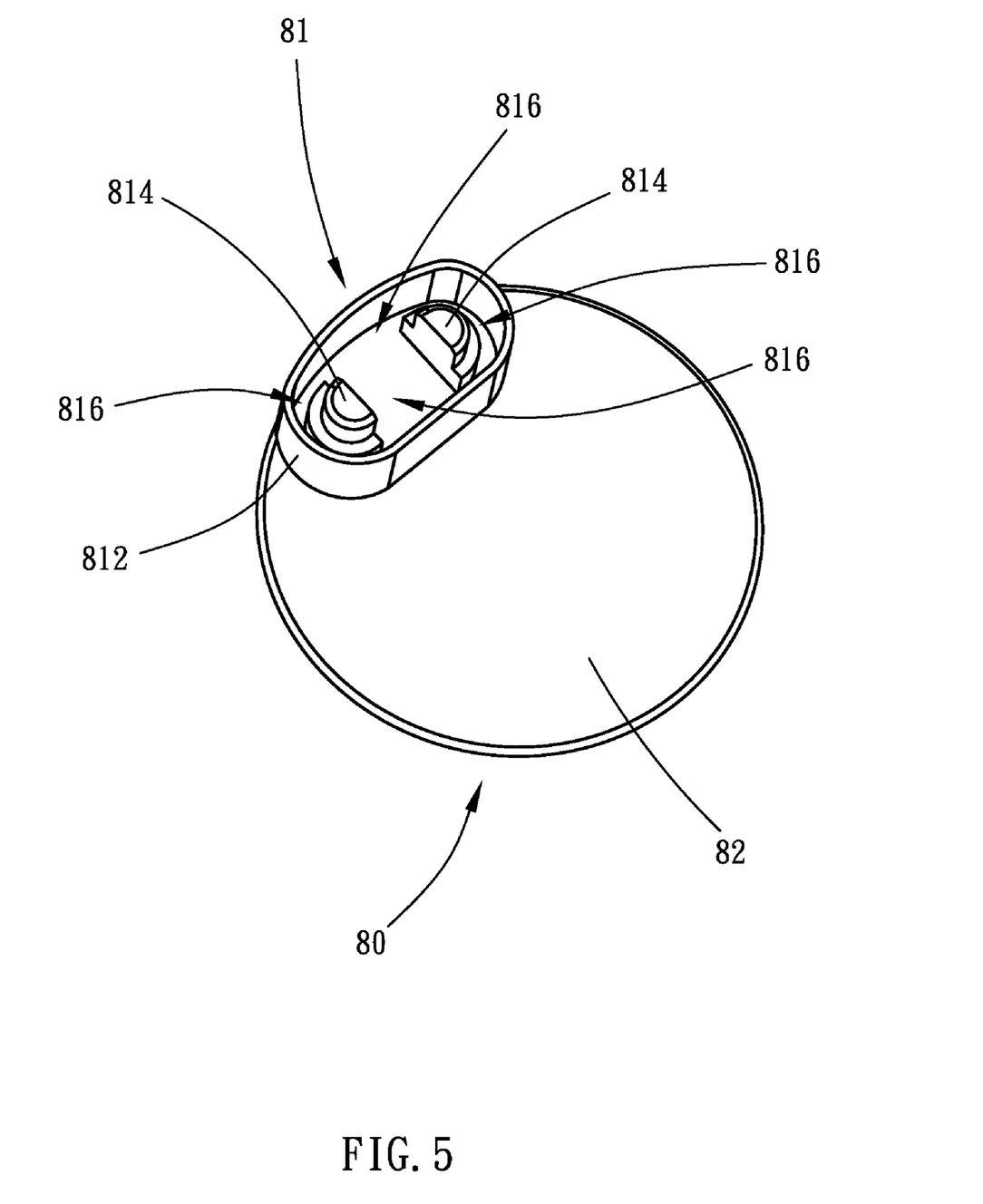
FIG. 5 is a bottom elevation of the water baffle of the aromatic nebulizing diffuser in accordance with the present invention.

Referring to FIG. 5 and FIGS. 2 and 6 again, the water baffle 80 comprises a pipe connector 81 and a tongue plate 82. The pipe connector 81 comprises a connector housing 812 and two retaining rods 814 suspending in the connector housing 812. The two retaining rods 814 and the connector housing 812 define at least one air jet 816 for reversing the flowing direction of the flow of air from the air outlet 642 of the air duct 64 toward the aromatic fluid in the fluid chamber 63. The two retaining rods 814 are inserted into the air outlet 642 of the air duct 64 so that the tongue plate 82 of the water baffle 80 extends transversely above the aromatic fluid in the fluid chamber 63. The pipe connector 81 of the water baffle 80 guides the flow of air from the air outlet 642 of the air duct 64 through the at least one air jet 816 toward the aromatic fluid in the fluid chamber 63, causing a part of the aromatic fluid to fly in drops, and therefore a fine mist of aromatic fluid droplets is produced.

The upper housing 90 has an opening 91 at the bottom side and a hole 92 at the top side opposite to the opening 91. By means of the bottom opening 91, the bottom side of the upper housing 90 is coupled to the top rim 52 of the lower housing 52. According to this first embodiment, the upper housing can be made of ceramic or light-transmissive ceramic to enhance output sound. Further, the upper housing 90, the water baffle 80 are made of a transparent or translucent material, such as glass, frosted glass, fiber glass, light-transmissive ceramic, plastics, acrylic or crystal in any of a variety of light colors that admits light.

When the aromatic nebulizing diffuser is electrically connected after filling of an aromatic fluid in the fluid chamber 63 of the fluid container 60, the ultrasonic oscillator 30 is turned on to oscillate, oscillating the aromatic fluid into a fine mist of aromatic fluid droplets. Further, the aforesaid water level sensor 31 is disposed above the elevation of the horizontal bottom wall 61 of the fluid container 60. When the fluid lever in the fluid chamber 63 dropped below the elevation of the top side of the water level sensor 31, the water level sensor 31 immediately provides a signal to the control circuit of the ultrasonic oscillator 30, causing the control circuit to cut off power supply from the ultrasonic oscillator 30, avoiding ultrasonic oscillator damage.

Further, when the light source 32 is turned on to emit light, light rays from the light source 32 go through the transparent or translucent upper housing 90, producing visual lighting effects. At the same time, currents of air are sucked from the atmosphere through the air vents 11 into the inside of the lower housing 50. The intake flow of air goes through the air duct 64 into the connector housing 812 of the pipe connector 81 of the water baffle 80 where the connector housing 812 guides the intake flow of air out of the at least one air jet 816 toward the aromatic fluid in the fluid chamber 63, causing a part of the aromatic fluid to fly in drops, and therefore a fine mist of aromatic fluid droplets is produced. The fine mist of aromatic fluid droplets thus produced flies out of the top hole 92 of the upper housing 90 to the outside open space. Therefore, the aromatic fluid droplets will not be detained in the upper housing 90 or forced back to the fluid chamber 63.

Figure 7:
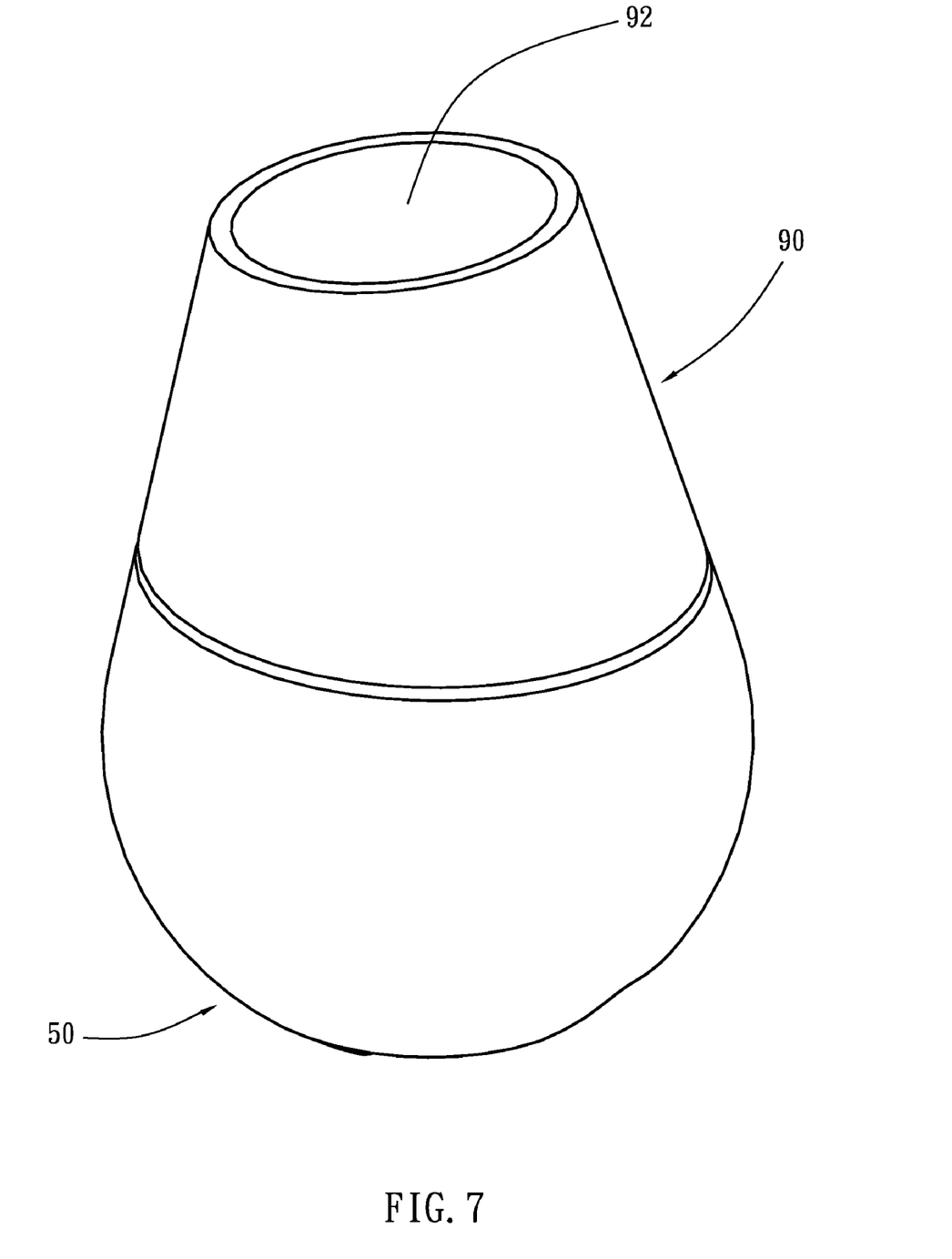
FIG. 7 is an elevational view of an aromatic nebulizing diffuser in accordance with a second embodiment of the present invention.
Figure 8:
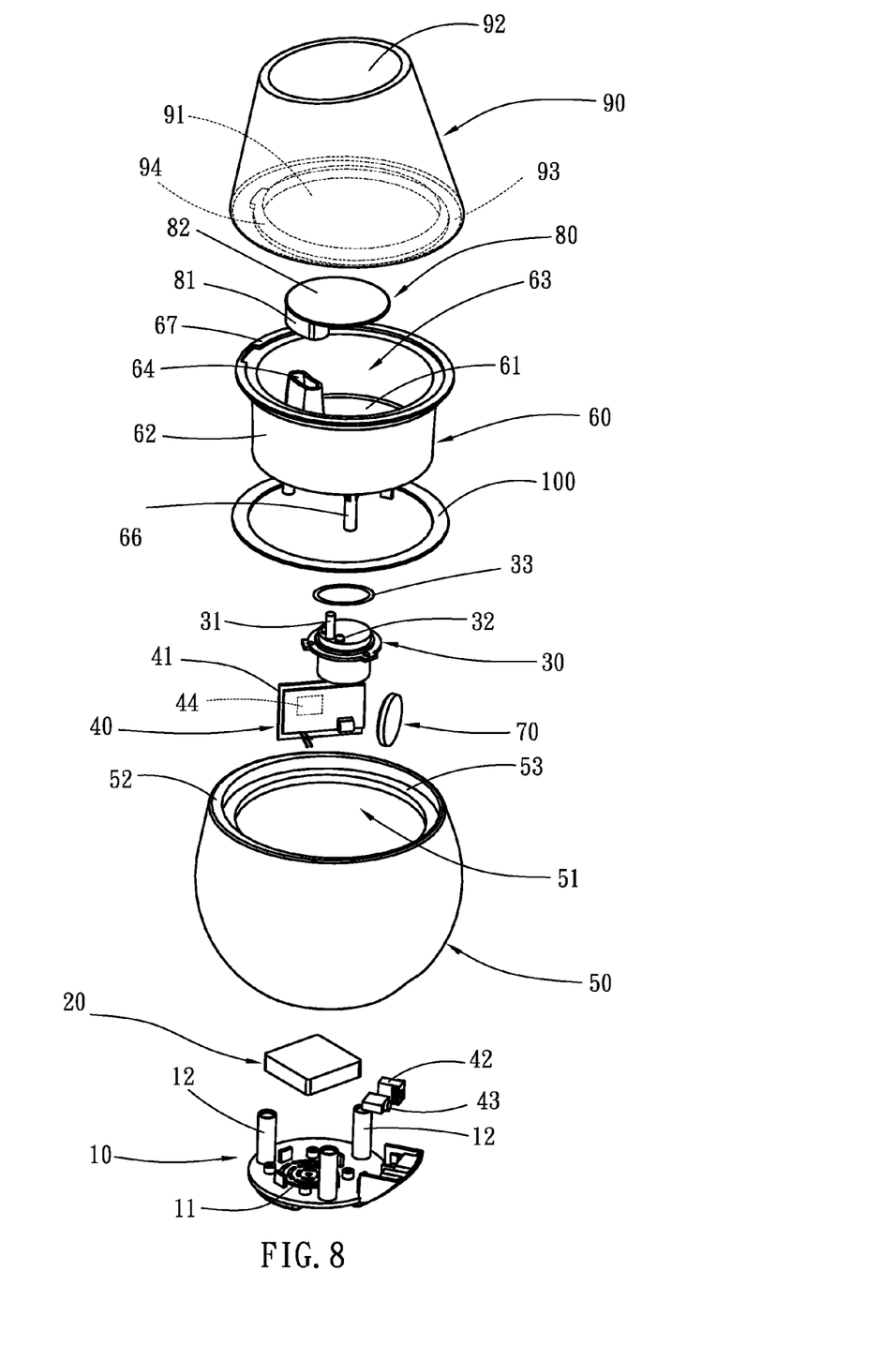
FIG. 8 is an oblique top exploded view of the aromatic nebulizing diffuser in accordance with the second embodiment of the present invention.
Figure 9:
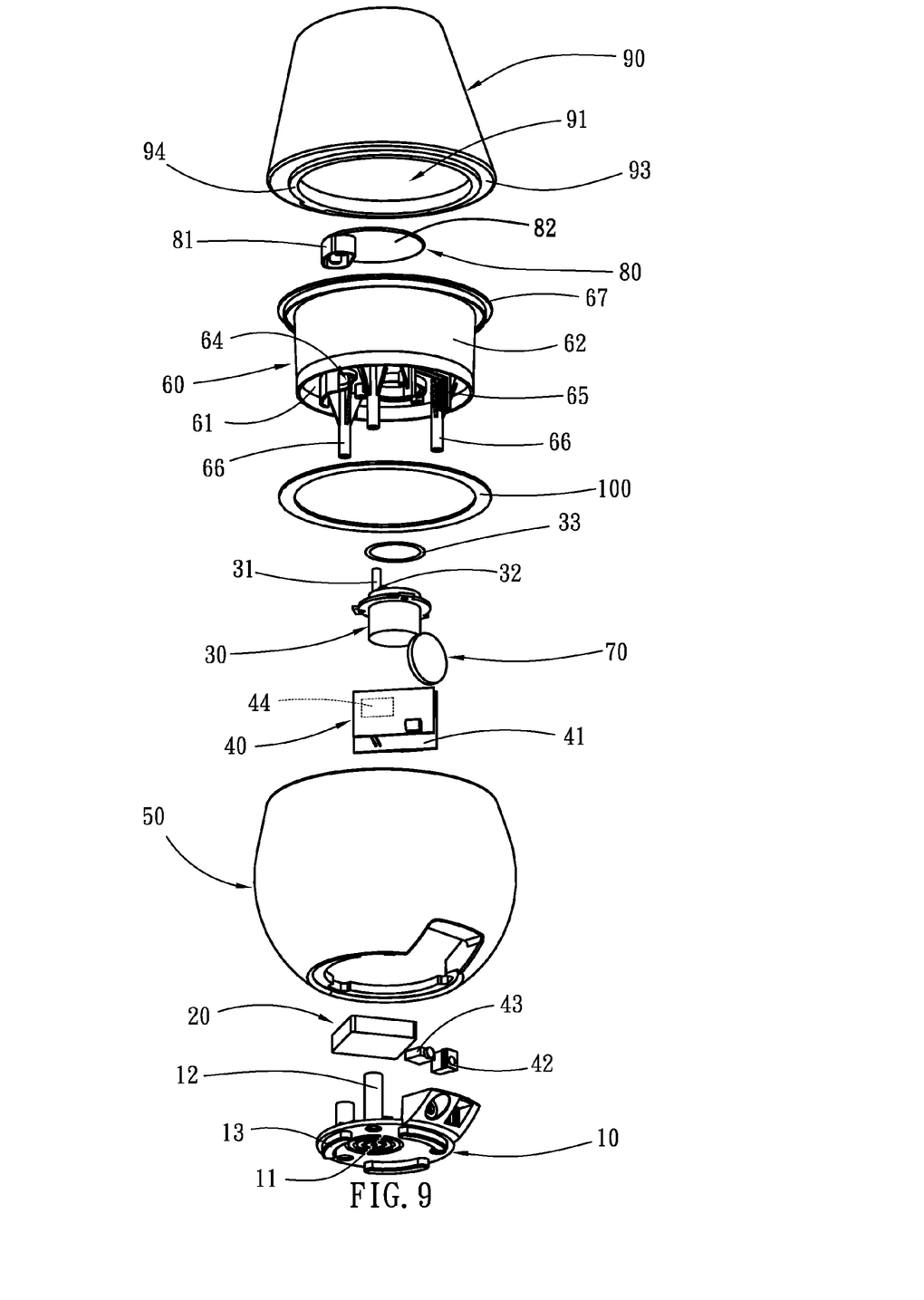
FIG. 9 is an oblique bottom exploded view of the aromatic nebulizing diffuser in accordance with the second embodiment of the present invention.

FIGS. 7~9 illustrate an aromatic nebulizing diffuser in accordance with a second embodiment of the present invention. According to this second embodiment, the upper housing 90, the water baffle 80 are made of a transparent or translucent material, such as glass, frosted glass, fiber glass, light-transmissive ceramic, plastics, acrylic or crystal in any of a variety of light colors that admits light.

When the aromatic nebulizing diffuser is electrically connected after filling of an aromatic fluid in the fluid chamber 63 of the fluid container 60, the ultrasonic oscillator 30 is turned on to oscillate, thereby oscillating the aromatic fluid into a fine mist of aromatic fluid droplets that flies out of the upper housing 90 through the top hole 92 into the outside open space. At the same time, the light rays from light source 32 go through the fine mist of aromatic fluid droplets and the peripheral wall of the upper housing 90, producing visual lighting effects.

Further, in the aforesaid first and second embodiments, the light source 32 comprises at least one LED (light emitting diode). The light emitting diode can be formed of a red LED chip, blue LED chip or green LED chip, or a combination thereof. The control circuit of the ultrasonic oscillator 30 also controls the operation of the light source 32, producing visual lighting effects. The ultrasonic oscillator 30 has the upper part thereof mounted in the mounting hole 68 on the horizontal bottom wall 61 of the fluid container 60 and sealed by a water seal ring 33 to prohibit leaking of the aromatic fluid out of the fluid container 60 through the mounting hole 68.

The fluid container 60 has a speaker holder 65 downwardly extended from the bottom side thereof to hold a speaker 70 that is electrically connected to the power control unit 40. This speaker mounting arrangement does not require an extra space for speaker, saving much installation space.

Further, the fluid container 60 has an annular top flange 67 radially extended from the topmost edge of the upright peripheral wall 62 and supported on the inside step 53 in the accommodation chamber 51 of the lower housing 50. Further, a water seal ring 100 is set in between the annular top flange 67 of the fluid container 60 and the inside step 53 of the lower housing 50. Because the annular top flange 67 of the fluid container 60 is supported on the water seal ring 100 at the top side of the inside step 53 of the lower housing 50, the water seal ring 100 effectively prohibits moisture in the fluid container 60 from leaking into the accommodation chamber 51 of the lower housing 50.

Further, because the speaker 70 is mounted in the vertically extended speaker holder 65 at the bottom side of fluid container 60 within the accommodation chamber 51 of the lower housing 50 but not closely attached to the air vents 11 on the base panel 10 for direct output of sound waves through the air vents 11 to the outside, the accommodation chamber 51 of the lower housing 50 works as a sound chamber to enhance output sound of the speaker 70, providing better sound effects.

Further, the power control unit 40 comprises a control circuit board 41, a power jack 42 and an audio jack 43. The power jack 42 is mounted on the base panel 10 and electrically connected to the control circuit board 41 for the connection of an external power source. The audio jack 43 is mounted on the base panel 10 and electrically connected to the control circuit board 41 for the connection of a cable from an external sound source (not shown) for output through the speaker 70 that is electrically connected to the control circuit board 41.

The aforesaid control circuit board 41 comprises a music control circuit 44 that controls the speaker 70 to output pre-recorded music, helping people to relief stress.

Further, the upper housing 90 has a bottom edge 93 extending around the bottom opening 91 and supported on the top rim 52 of the lower housing 50, and a bottom flange 94 perpendicularly downwardly extended from the bottom edge 93 and stopped against the fluid container 60. Thus, the upper housing 90 is detachable, facilitating cleaning.

The base panel 10 further has a plurality of foot members 13 located on the bottom side. When the aromatic nebulizing diffuser is placed on a flat surface, the foot members 13 keep the air vents 11 of the base panel 10 above the flat surface at a distance, facilitating ventilation and heat dissipation. Thus, the electric fan 20 can suck in air from the atmosphere into the inside of the aromatic nebulizing diffuser smoothly, and output sound waves of the speaker 70 can be driven out of the lower housing 50 through the air vents 11 of the base panel 10 effectively.

Further, the fluid to be filled in the fluid container 60 can be water, essential oil, flower essences, rosemary oil, perfume or natural plant extracts, or their combination.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An aromatic nebulizing diffuser, comprising:
   a base panel, said base panel comprising a plurality of air vents cut through top and bottom walls thereof and a plurality of tubular upright posts perpendicularly upwardly extended from the top wall;
   an electric fan mounted on said base panel;
   an ultrasonic oscillator for generating oscillation energy, said ultrasonic oscillator with control circuit function;
   a water level sensor arranged on a top side of said ultrasonic oscillator and controllable to work by said ultrasonic oscillator;
   a power control unit electrically connected to said electric fan, said ultrasonic oscillator, said water level sensor and a light source to provide the necessary working voltage;
   a lower housing surrounding said base panel and defining with said base panel an accommodation chamber that accommodates said power control unit, said electric fan, said ultrasonic oscillator, said water level sensor and said light source, said lower housing having a top rim;

a fluid container accommodated in said accommodation chamber of said lower housing, said fluid container comprising a horizontal bottom wall, a vertical peripheral wall, a fluid chamber surrounded by the horizontal bottom wall and the vertical peripheral wall, an air duct suspending in said fluid chamber, a plurality of bottom mounting rods perpendicularly downwardly extended from the horizontal bottom wall and respectively detachably plugged into said tubular upright posts of said base panel, and a mounting hole cut through the horizontal bottom wall at the center and accommodating said ultrasonic oscillator; and an upper housing, said upper housing comprising a bottom opening disposed at a bottom side thereof and coupled to the rim of said lower housing and a top hole at a top side thereof opposite to said bottom opening.

2. The aromatic nebulizing diffuser as claimed in claim 1, wherein said fluid container comprises a speaker holder downwardly extended from the horizontal bottom wall thereof and holding a speaker that is electrically connected to said power control unit.

3. The aromatic nebulizing diffuser as claimed in claim 1, wherein said power control unit comprises a circuit board, a power jack mounted on said base panel and electrically connected to said control circuit board for the connection of an external power source and an audio jack mounted on said base panel and electrically connected to said control circuit board to provide a sound source signal.

4. The aromatic nebulizing diffuser as claimed in claim 1, wherein the light source being arranged on the top side of said ultrasonic oscillator and controllable by said ultrasonic oscillator to emit light.

5. The aromatic nebulizing diffuser as claimed in claim 1, wherein said lower housing comprises an inside step in said accommodation chamber; said fluid container comprises an annular top flange radially extended from the topmost edge of the upright peripheral wall thereof and supported on the inside step in said accommodation chamber of said lower housing and sealed with a water seal ring that is set in between the annular top flange of said fluid container and the inside step of said lower housing; said ultrasonic oscillator has an upper part thereof mounted in the mounting hole on the horizontal bottom wall of said fluid container and sealed with a water seal ring.

6. The aromatic nebulizing diffuser as claimed in claim 2, wherein said fluid container further comprises a music control circuit for controlling said speaker to output pre-recorded music.

7. The aromatic nebulizing diffuser as claimed in claim 1, wherein said upper housing comprises a bottom edge extending around the bottom opening thereof and supported on the top rim of said lower housing, and a bottom flange perpendicularly downwardly extended from the bottom edge and stopped against said fluid container.

8. The aromatic nebulizing diffuser as claimed in claim 1, wherein said upper housing is made of a transparent material.

9. The aromatic nebulizing diffuser as claimed in claim 1, wherein said upper housing is made of a light transmissive material.

* * * * *